| United States Patent [19] | [11] Patent Number: 5,011,926 |
| Knifton | [45] Date of Patent: Apr. 30, 1991 |

[54] NICKEL-BASED DUAL CATALYST SYSTEMS EFFECTIVE IN SUPPRESSING CARBON DIOXIDE FORMATION DURING DIETHYLENE GLYCOL AMINATION

[75] Inventor: John F. Knifton, Austin, Tex.

[73] Assignee: Texaco Chemical Company, White Plains, N.Y.

[21] Appl. No.: 543,017

[22] Filed: Jun. 25, 1990

[51] Int. Cl.$^5$ .......................................... C07D 295/023
[52] U.S. Cl. .................................... 544/106; 564/480
[58] Field of Search .......................................... 544/106

[56] References Cited

U.S. PATENT DOCUMENTS 4,508,896 4/1985 Templeton .......................... 544/106

*Primary Examiner*—Robert W. Ramsuer
*Attorney, Agent, or Firm*—Jack H. Park; Kenneth R. Priem; Cynthia L. Kendrick

[57] ABSTRACT

Disclosed is a process for simultaneously producing morpholine and DIGLYCOLAMINE® amine while suppressing $CO_2$ formation comprising the steps of:
reacting diethylene glycol with ammonia in the presence of added hydrogen over a dual nickel-based catalyst comprising a nickel-copper-chromium oxide mix in combination with nickel-on-alumina, a
isolating said morpholine compound and said DIGLYCOLAMINE® amine compound from the reaction products.

9 Claims, No Drawings

NICKEL-BASED DUAL CATALYST SYSTEMS EFFECTIVE IN SUPPRESSING CARBON DIOXIDE FORMATION DURING DIETHYLENE GLYCOL AMINATION

This invention relates to the practice of making morpholine from diethylene glycol by an amination reaction. More particularly this invention relates to the use of a novel nickel-based, dual-catalyst system for the selective amination of diethylene glycol (DEG) to morpholine plus DIGLYCOLAMINE® amine, 2-(2-aminoethoxy)-ethanol, (DGA) wherein the coproduction of $CO_2$ is significantly suppressed. Surprisingly, it has been found that only certain combinations of nickel-based dual catalyst systems are effective in suppressing $CO_2$ formation during morpholine service.

BACKGROUND OF THE INVENTION

The practice of making morpholine plus DIGLYCOLAMINE® amine from diethylene glycol and ammonia over an amination catalyst is well-known in the art (see, for example, U.S. Pat. No. 3,151,112 (1964). The reaction is generally run in an aqueous environment. The indication is that better productivity could be obtained using an anhydrous feed, since water acts as a diluent and takes up space in the reactor. Whether run under aqueous or anhydrous feed conditions, there are two principal gaseous by-products, methane and carbon dioxide. Under aqueous conditions most of the $CO_2$ is absorbed into the $H_2O$. Under anhydrous feed conditions, even though water is a reaction by-product (e.g. see Equations 1 and 2), the $CO_2$ will readily react with the excess ammonia to form ammonium bicarbonate and/or ammonium carbamate, both of which in the absence of adequate water diluent, will form solids which precipitate downstream of the amination reactor, in the heat exchanger, etc., causing additional unit maintenance costs and engineering problems. It would be extremely advantageous if it were possible to operate a morpholine/DIGLYCOLAMINE® process using anhydrous diethylene glycol/ammonia feed in such a fashion that $CO_2$ by-product formation was lowered to below, or close to, threshold levels (i.e. <50 ppm). Such a condition might be achieved by converting said $CO_2$ to methane (Equation 3), possibly by introducing a methanation catalyst into the process unit, downstream of the diethylene glycol amination step. Particularly useful would be a methanation catalyst that:

(a) Lowers the $CO_2$ concentration in the morpholine/DIGLYCOLAMINE® amine product effluent to threshold levels.

(b) Is stable in the high pH, amine, environment of the morpholine/DIGLYCOLAMINE® product effluent.

(c) Remains an active methanation catalyst in said environment for extended periods, particularly at the temperature of DEG amination (190°–250° C).

(d) Does not convert the desired morpholine and DIGLYCOLAMINE® to unwanted by-products, as a result of catalyzing secondary reactions in the crude product effluent.

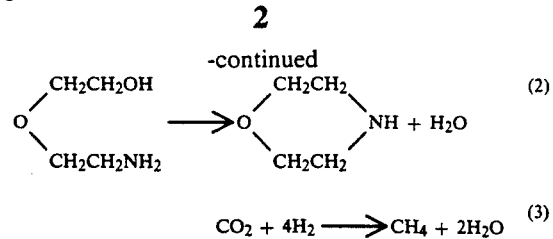

$$CO_2 + 4H_2 \longrightarrow CH_4 + 2H_2O \quad (3)$$

No art has been found dealing with a provision for converting by-product $CO_2$ to methane when said $CO_2$ is present in an amination product effluent, particularly where the $CO_2$ is present in a morpholine/DIGLYCOLAMINE® amine product mix resulting from the amination of diethylene glycol (DEG) with ammonia.

It is known that carbon dioxide can be converted into methane by reduction with four moles of hydrogen (Equation 3). This is called the "Sabatier reaction". The mechanism for the reaction is not clear and early researchers assumed the reaction occurred in stages, however Bardet and Trambouze reported in work in C. R. Hebd. Seances. Acad. Sci., Ser. C. 288 (1979), 101, that it appeared $CO_2$ methanation had its own mechanism, distinct from CO methanation, and that $CO_2$ methanation occurs faster and at lower temperatures than methanation of CO. Heterogeneous catalysts have proven best for this process, see "Carbon Dioxide Activation by Metal Complexes," by A. Behr, Chapter 4, p. 85 (1988).

The mechanism for hydrogenation of $CO_2$ on nickel is discussed in an article titled, "Hydrogenation of $CO_2$ on Group VIII Metals II. Kinetics and Mechanism of $CO_2$ Hydrogenation on Nickel," G. D. Weatherbee, et al., J. Catal., 77, 460–472 (1982). The rate of $CO_2$ hydrogenation was measured as a function of $H_2$ and $CO_2$ partial pressures at 500–600° K, 140 kPa and 30,000–90,999 h$^{-1}$. The data indicated the rate of $CO_2$ hydrogenation is moderately dependent on $CO_2$ and $H_2$ concentrations at low partial pressures but essentially concentration independent at high partial pressures. Under typical conditions CO was observed as a product of the reaction at levels determined by quasi-equilibrium between surface and gas phase CO species. Addition of CO to the reactants above this equilibrium level caused a significant decrease in the rate of $CO_2$ hydrogenation apparently as a result of product inhibition.

These authors set forth the following table which in their view summarized the mechanism for $CO_2$ hydrogenation and accounted for the observations of this study and other recent studies.

| Proposed Sequence of Elementary Steps in $CO_2$ Methanation$^a$ |
|---|
| Reaction |

$$H_2(g) + S \underset{k_{-1}}{\overset{k_1}{\rightleftharpoons}} 2H—S$$

$$CO(g) + 2S \underset{k_{-2}}{\overset{k_2}{\rightleftharpoons}} CO—S + O—S$$

$$CO—S \underset{k_{-3}}{\overset{k_3}{\rightleftharpoons}} CO(g) + S$$

$$CO—S \underset{k_{-4}}{\overset{k_4}{\rightleftharpoons}} C—S + O—S$$

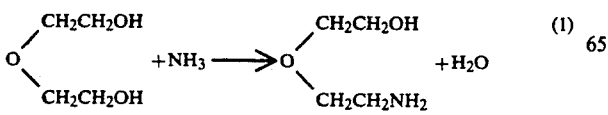

-continued

Proposed Sequence of Elementary Steps in $CO_2$ Methanation[a]

Reaction

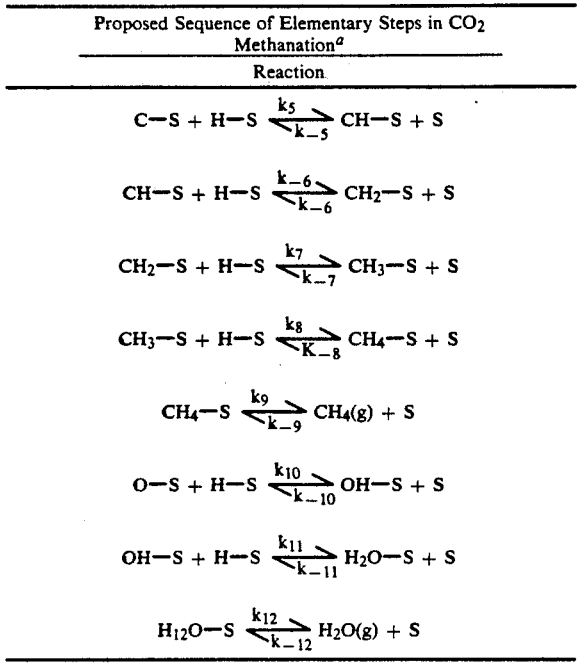

[a] S refers to a surface site.

The authors also noted that kinetic studies of methanation in their laboratory provided evidence that there are several mechanistic regimes involving different rate controlling steps, the importance of which depends mainly on temperature.

The authors proposed that at moderate reaction temperatures (525–575° K, CO dissociation appeared to be rate controlling while hydrogenation of carbon apparently controlled at higher reaction temperatures (>575° K). This suggested that CO and $CO_2$ methanation rates on nickel are both controlled by CO dissociation at moderate reaction temperatures (525–575° K), a hypothesis consistent with the observation of nearly identical specific reaction rates in $CO_2$ and CO methanation on $Ni/SiO_2$. The authors further proposed that it is possible for the two reactions to follow similar paths and still have different rate determining steps.

$CO_2$ Methanation catalysts are discussed in an article titled "Highly Active Catalysts For $CO_2$ Methanation To Provide The Second Reactor Of Two Stage Process For High BTU SNG Synthesis", A. D. Tomsett, et al., Applied Catal. 26 391 (1986). This investigation was made in the context of identifying highly active catalysts suitable for the second of two stages in a process for conversion of syngas to high BTU substituted natural gas. It was found that supported $Ni-La_2O_3-Ru$ catalysts are effective for $CO_2$ methanation. These catalysts provided high activity and complete conversion of $CO_2$ to methane at as low a temperature as 250° C.

It was concluded that the high activity of the $Ni-La_2O_3-Ru$ catalysts is mainly ascribable to the large number of active sites.

It is known that methanation reactions are the reverse of reforming reactions. The methanation reactions are exothermic and, therefore, since a methanator typically operates in the temperature range of 300–400° C the CO and $CO_2$ at the inlet should be carefully monitored to avoid damage to catalyst and vessel, see Kirk-Othmer, Encyclopedia of Chem. Tech., 3rd Edition, Vol. 2, p. 494.

Related art includes an investigation discussed in an article titled "Hydrogenation of $CO_2$ over Co/Cu/K Catalysts", H. Baussart, et al., J. Chem. Soc. Faraday Trans. I, 83, 1711 (1987). Here Co, K and Cu, as components of catalysts were investigated for the specific roles each played in the hydrogenation of $CO_2$. The results indicated, inter alia that a steady state was reached after ca. 30 hours of activation. It was found that the presence of cobalt favored the formation of alkanes, and that the presence of potassium favored the formation of CO resulting from a reverse water-gas shift reaction ($CO_2+H_2\rightarrow CO+H_2O$). Further, it appeared the presence of copper in Russell catalysts increased the activity and the selectivity for $CH_4$ and reduced the number of products.

There is a report on results of investigations into potassium-promoted nickel catalysts by T. K. Campbell, et al., Applied Catal., 50, 189 (1989). It was found potassium did not increase higher hydrocarbon or olefin selectivity, but it changed the $CH_4/CO$ product distribution. It was also found that potassium did not change $CO_2$ methanation mechanism and the mechanism appeared to be quite similar to that for CO hydrogenation. This paper presented steady-state kinetic data for $CO_2$ hydrogenation on $Ni/SiO_2$ and $Ni/SiO_2-Al_2O_3$ catalysts for a range of potassium concentrations. It was reported that hydrogenation reactions of $CO_2$ and CO on potassium promoted nickel catalysts are similar:

The activities and selectivities depend significantly on the support.

The rate of methanation on $Ni/SiO_2$ decreases exponentially for both reactions with potassium addition.

The rate of methanation on $Ni/SiO_2-Al_2O_3$ initially increases for both reactions with potassium addition.

In U.S. Pat. No. 4,508,896 there is described a process for simultaneously producing a 2-(2-aminoalkoxy)alkanol compound and a morpholine compound by contacting oxydialkanol with ammonia in the presence of a hydrogenation/dehydrogenation catalyst. In that process a hydrogenation catalyst was used which comprised about 60–85 mole % nickel, 14–37 mole % copper and 1–6 mole % chromium calculated on an oxide-free basis. This work does not address the problem of a methanation catalyst, $CO_2$ production and its effect in lowering productivity.

Preoxidized rhodium was studied as a catalyst for methanation of carbon monoxide in an article titled "Methanation of Carbon Dioxide over Preoxidized Rhodium", A. Amariglio, et al., J. Catal., 81 247 (1983). The authors confirmed that according to their experiments preoxidation of Rh caused a dramatic enhancement of its activity in the methanation of $CO_2$. They estimated preoxidation allowed the rate to be increased by a factor of 100 at the lowest estimate. The authors also concluded that the deactivation, observed upon prolonged exposures to $H_2$, must be ascribed to the depletion of the preincorporated oxygen.

From the art available it is evident that there are many factors and multiple variables involved in the methanation of $CO_2$, such that it would be difficult to identify a catalyst which would promote methanation at low temperatures (<250° C) and high pH within a dual catalyst system where the conditions are geared toward a primary reaction, such as amination.

It would constitute a distinct advance in the art if a catalyst system were available whereby $CO_2$ formation could be suppressed during morpholine/DGA amine processing by amination of DEG under anhydrous conditions. It has been discovered that not just any methanation catalyst could be used in this fashion because of certain critical factors, particularly those outlined SUPRA.

Unexpectedly it has been discovered that a dual catalyst system comprising a nickel-copper-chromium oxide in conjunction with an oxide-supported nickel catalyst is very effective for selective amination of DEG to morpholine plus DIGLYCOLAMINE ® amine while at the same time significantly suppressing the coproduction of $CO_2$.

SUMMARY OF THE INVENTION

According to the broad aspect of this invention morpholine and DIGLYCOLAMINE ® amine are simultaneously produced while at the same time $CO_2$ production is substantially suppressed by a process comprising contacting diethylene glycol, ammonia and hydrogen in the presence of a dual catalyst comprising nickel-copper-chromium oxide in conjunction with an oxide-supported nickel catalyst at a temperature of 150° C to 300° C and pressure ranging from 200 to 5000 psi under anhydrous feed conditions and in the presence of a substantial quantity of hydrogen, and recovering the products.

DETAILED DESCRIPTION OF THE INVENTION

According to the preferred embodiment, oxydiethanol, also known as diethylene glycol, is contacted with ammonia and hydrogen in the presence of a catalytically effective amount of a dual catalyst system comprising an amination/hydrogenation/dehydrogenation catalyst and a methanation catalyst, wherein the amination/hydrogenation/dehydrogenation catalyst consists of an oxide of 60 to 85 mole % nickel, about 14 to 37 mole % copper and 1 to 6 mole % chromium, and the methanation catalyst comprises an oxide-supported nickel catalyst.

The reaction takes place in a continuous process and contacting of the reactants is accomplished at a temperature of from 150° C to about 300° C and at a pressure of about 200 psig to about 5000 psig. The molar ratio of ammonia to oxydiethanol is preferably from about 4:1 to about 8:1 and the space velocities of the liquid feed material, i.e. ammonia and oxydiethanol, are from about 1g of liquid feed per hour per milliliter of catalyst to about 6g of liquid feed per hour per milliliter of catalyst. The recovered reaction product, consisting primarily of DIGLYCOLAMINE ® amine and morpholine, is recovered from the resultant crude reaction product by conventional means such as distillation, extraction and the like.

The oxydialkanol compound that can be utilized in practicing the instant invention can be of the general formula:

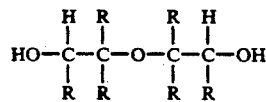

wherein each R is, independently, a hydrogen or a lower alkyl radical, such as, for example, methyl, ethyl or the like. The examples demonstrate the effectiveness of oxydiethanol or ethylene glycol.

The catalyst for amination of diethylene glycol which may be employed in practicing the invention may generally be characterized as an amination catalyst or as an amination/hydrogenation/dehydrogenation catalyst. Examples include copper, nickel, chromium, cobalt, manganese, molybdenum, palladium, platinum, rhodium, oxides of such metals and mixtures thereof. A particularly preferred catalyst is characterized by having the composition calculated in mole % of from about 60–85% nickel, 14–37% copper and 1–6% chromium with the preferred proportions being about 72–78% nickel, 20–25% copper and 1–3% chromium. A greatly preferred hydrogenation catalyst is one in which the active components consist essentially of about 75 mole % nickel, about 23 mole % copper and about 2 mole % chromium in the form of an oxide.

A commercially available amination/hydrogenation catalyst fitting this description is Engelhard Ni-2715 T 3/16". Engelhard Ni-2715 is a nickel-based catalyst produced by Engelhard which contains a nickel-copper-chromium oxide.

As mentioned only certain combinations of nickel-based dual catalyst systems are effective in suppressing $CO_2$ formation during morpholine service and it has been surprisingly discovered in the instant invention that an effective methanation catalyst in combination with the nickel-copper-chromium oxide catalyst, are oxide-supported nickel catalysts. Said oxide supports may be selected from the oxides of the Group II, III and IV elements. The preferred supports include magnesia, alumina, silica, zirconia and titania, as well as mixtures thereof. The preferred support is alumina.

The nickel may be added to said support by any of the usual methods and said formulated catalyst may comprise from 10 to 80 wt % nickel. The preferred nickel loading is 40 to 60 wt %, and the preferred catalyst formulation comprise 40 to 60 wt % nickel-on-alumina. Suitable commercially-available catalysts include Engelhard D-4132 and Calsicat Catalysts E331, E475 and E217.

Said combination of nickel-based dual catalysts may be used in any proportions except that preferably the nickel-copper-chromium oxide catalyst should contact the diethylene glycol/ammonia feed first, in order to achieve the desired amination (Equations 1 and 2), then after the desired DEG conversion is achieved, the reactant product should contact the oxide-supported nickel catalyst in order to significantly lower the $CO_2$ effluent concentration (through Reaction 3).

A particularly effective ratio of nickel-copper-chromium oxide catalyst to oxide-supported nickel catalyst is in the range 1:1 to 10:1 by volume. The accompanying examples illustrate such a ratio range. A particularly preferred dual nickel catalyst combination is Engelhard Ni-2715 T 3/16" and Engelhard D-4132 E 1/6".

The ratio of reactant, i.e. the ratio of ammonia to oxydiethanol, or other oxydialkanol used in this process is 1:1 to about 10:1 although a molar excess of ammonia produces increased yields of the morpholine product. Optimum yields are obtained when the molar ratio of ammonia to oxydiethanol is about 6:1.

The space velocities of the feed, namely, the ammonia and the glycol, may vary from about 1 gram of the liquid feed/hour/milliliter of catalyst, to about 6 grams of liquid feed/hour/milliliter of catalyst. As noted above, the temperature range for the present invention is between 150° C and 300° C, the preferred range is 200° to 250° C, depending upon the reactant ratios utilized.

Those skilled in the art will realize that an outstanding advantage of the instant process resides in the fact that the relative yields of morpholine and DIGLYCOLAMINE ® amine can be varied by a slight variation of reaction conditions while the production rate of the combined products remains high. Thus, one can achieve a substantial yield of 2-(2-aminoethoxy)ethanol while simultaneously maintaining morpholine production rates comparable to or better than those obtained by previously known methods.

The process should be carried out in a reductive atmosphere using hydrogen for commercial operations. Although small amounts of hydrogen are present during the reaction from the catalyst materials and as a by-product, it is preferred that hydrogen be added in the feed system in order of achieved $CO_2$ methanation (Equation 3) and to maintain catalytic activity. The quantity of hydrogen necessary for the practice of this invention is generally in the range of from 0.1 to 1000 liters (1) per lb of DEG converted, the preferred range is from 10 to 200 liters $H_2$ per lb of DEG converted. Such a ratio is illustrated in the accompanying examples.

The quantity of $CO_2$ produced in this morpholine/DIGLYCOLAMINE ® amine process is normally measured in terms of parts per million (ppm) in the effluent product and is expressed in terms of lbs of $CO_2$ generated per 100M lb of DEG converted.

The accompanying examples illustrate the following:
(1) In Example I, the generation of morpholine plus DIGLYCOLAMINE ® (DGA ® amine) is demonstrated using a dual, nickel-based, catalyst system comprising a nickel-copper-chromium oxide catalyst (Engelhard Ni-2715 T 3/16") in combination with a nickel-on-alumina (Engelhard D-4132 E 1/16") to achieve:
85% DEG conversion at 220° with 133 lb $CO_2$ per 100 lb DEG converted.
(2) In Example 3, the same catalyst combination at a higher hydrogen flow rate of 90 l/hr provided:
77% DEG conversion at 215° C with an average of just 35 lb $CO_2$ per 100M lb DEG converted.
(3) By comparison, in comparative Example A, using only Ni-2715 T 3/16"
82% DEG conversion at 220° C gave 499 lb $CO_2$ per 100M lb converted.
We conclude that:
(a) Comparing Examples 1 and 4, the $CO_2$ made using the nickel dual catalyst system is cut from 499 to 133 lb per 100 lb DEG converted, a factor of 3.75.
(b) Comparing Examples 3 and 4, the $CO_2$ made using the nickel dual catalyst system and a higher hydrogen flow is cut from 499 to an average of 34 lb per 100M lb DEG converted, a factor of ca. 15.
(4) Other oxide-supported nickel catalysts, in combination with Ni-2715 T 3/16", are effective in lowering the $CO_2$ effluent production to the range of 12–41 lb $CO_2$/100M lb DEG converted (see Examples 5–7), while a nickel-copper-chromium on alumina catalyst was generally ineffective (see Comparative Example B).
(5) The Ni-2715 T 3/16"+D4132 E 1/16" combination is effective in substantially lowering $CO_2$ production over 500 hours of operation, where the volume ratio of the two catalysts is ca. 2.7:1 (Example 8).

EXAMPLE 1

To a 500cc capacity plug-flow reactor fitted with heating, cooling and pressure control devices, and constructed of stainless steel, was charged a combination of 400cc of pelleted nickel-copper-chromium oxide catalyst (in which the active components consisted essentially of 71.2 wt % Ni, 12.3 wt % Cu and 73.3% reduced Ni) and 150cc of extruded nickel-on-alumina catalyst (47.5% Ni). The pelleted nickel-copper-chromium oxide catalyst was placed in the bottom section of the reactor and the nickel-on-alumina at the top.

Diethylene glycol (1.2 lbs/hr), ammonia (2.4 lbs/hr) and hydrogen (35 liters/hr) were fed separately to the reactor system from the bottom of the reactor, in an upflow mode, through the catalyst bed of the reactor. The reactor effluent was cooled, depressured and the gaseous and liquid products analyzed. After a 48-hour prerun period to establish steady state conditions, the performance of the dual-catalyst system was tested at a series of operating temperatures (210–240° C) while maintaining a reactor back-pressure of 2200 psi.

Data and results from the run are summarized in Table I. It may be noted that in this run:

At an operating temperature of 210° C, the DEG conversion was 69.9% and the $CO_2$ production was 63 lbs per 100M lb of DEG converted. While at 220° C, the DEG conversion was 8.6.0% and the $CO_2$ production was 133 lbs per 100M lb DEG converted.

TABLE I

| Reaction Temp. (°C.) | DEG Conversion (%) | Yield (%) Basis DEG Converted | | Effluent Conc. $CO_2$ (ppm) | $CO_2$ (lbs) per 100 M lbs. DEG Converted |
| --- | --- | --- | --- | --- | --- |
| | | Morpholine | DGA | | |
| 210 | 69.9 | 62.4 | 34.0 | 45 | 63 |
| 220 | 86.0 | 77.1 | 18.9 | 140 | 133 |
| 230 | 94.1 | 84.5 | 9.2 | 340 | 349 |
| 240 | 96.4 | 80.8 | 7.4 | 1110 | 1117 |

TABLE II

| Time On Stream Hrs. | DEG Conversion (%) | Yield (%) Basis DEG Converted | | Effluent Conc. $CO_2$ (ppm) | $CO_2$ (lbs) per 100 M lbs. DEG Converted |
| --- | --- | --- | --- | --- | --- |
| | | Morpholine | DGA | | |
| 24 | 65.6 | 58.7 | 38.0 | 118 | 170 |
| 48 | 65.9 | 58.7 | 38.0 | 130 | 201 |
| 72 | 68.0 | 60.1 | 36.7 | 143 | 213 |
| 100 | 67.1 | 57.8 | 38.6 | 165 | 251 |

EXAMPLE 2

Following the operation procedures of Example 1 and using the same nickel-based dual catalyst system of nickel-copper-chromium oxides (400cc, bottom of reactor) and nickel-on-alumina (150cc, top of reactor) diethylene glycol amination was conducted at the same feed rates and back pressure, but at an operating temperature of 215° C.

Data and results from this four-day run are summarized in Table II. It may be noted that in this experiment the average DEG conversion was ca. 66.7%, while the $CO_2$ production was an average 209 lbs per 100M lb of DEG converted.

EXAMPLE 3

Following the operating procedures of Example 1 and using the same nickel-based dual catalyst system of nickel-copper-chromium oxides (400cc, bottom of the reactor) and nickel-on-alumina (150cc, top of reactor), diethylene glycol amination was conducted at the same DEG and ammonia feed rate, but at a significantly higher hydrogen feed rate of 90 liters/hr. Again, the operation temperature and pressure were 215° C and 2200 psi, respectively.

Data and results from this four-day run are summarized in Table III. It may be noted that in this experiment the average DEG conversion is ca. 77%, but the $CO_2$ production is now only 34 lbs per 100M of DEG converted.

TABLE III

| Time On Stream (Hrs) | DEG Conversion (%) | Yield (%) Basis DEG Converted | | Effluent Conc. $CO_2$ (ppm) | $CO_2$ (lbs) per 100 M lbs. DEG Converted |
|---|---|---|---|---|---|
| | | Morpholine | DGA | | |
| 24 | 78.1 | 73.7 | 18.3 | 25 | 28 |
| 48 | 78.0 | 77.8 | 15.9 | 40 | 48 |
| 72 | 75.6 | 72.6 | 17.9 | 20 | 26 |
| 100 | 76.4 | 76.0 | 15.3 | 23 | 32 |

COMPARATIVE EXAMPLE A

Following the operating procedures of Example 1, the 550 cc plug flow reactor was filled with the nickel-copper-chromium oxide catalyst alone and diethylene glycol amination was conducted at feed rates of 1.2 lb/hr DEG, 2.4 lb/hr of ammonia and 35 liters/hr of hydrogen. Again, the operating temperature and pressure were 220° C and 2200 psi, respectively.

Analysis of the liquid and gas products shows:
DEG Conversion—82%
Yield of Morpholine—65.3%
Yield of DGA—30.3%
Effluent Conc. $CO_2$—689 ppm
$CO_2$ per 100M lbs DEG Converted—499 lbs.

EXAMPLE 4

Following the operating procedures of Example 1, the same nickel-based dual catalyst system was employed but in different proportions. In this case the reactor was charged with 475cc of the nickel-copper-chromium oxides and with 75cc of the nickel-on-alumina at the top of the reactor. Two hydrogen flow rates were employed (35 and 90 liters per hour) and the operating temperature ranged from 210-230° C. The results are summarized in Table IV.

It may be noted that at 90 liters/hr $H_2$, the $CO_2$ production was only 20-28 lbs/100M lb DEG conv., when the operating temperature was in the range 210-220° C.

TABLE IV

| Reaction Temp. (°C.) | $H_2$ Feed Rate (l/hr) | DEG Conv. (%) | Yield (%) Basis DEG Converted | | Effluent Conc. $CO_2$ (ppm) | $CO_2$ (lbs) per 100 M lbs DEG Converted |
|---|---|---|---|---|---|---|
| | | | Morpholine | DGA | | |
| 210 | 35 | 79.7 | 63.6 | 31.1 | 130 | 168 |
| 215 | 35 | 88.6 | 73.1 | 21.1 | 230 | 265 |
| 220 | 35 | 93.1 | 79.1 | 14.9 | 370 | 407 |
| 230 | 35 | 98.3 | 88.2 | 5.2 | 940 | 987 |
| 210 | 90 | 79.6 | 71.7 | 17.0 | 19 | 24 |
| 215 | 90 | 91.0 | 77.5 | 6.7 | 19 | 20 |
| 220 | 90 | 95.8 | 78.0 | 4.1 | 30 | 28 |

EXAMPLES 5–7

Following the operating procedures of Example 1, different nickel-based dual catalyst systems were employed over a range of operating hydrogen feed rates (35–90 liters/hr) and temperatures (210–240° C. In each case 400cc of the nickel-copper-chromium oxide catalyst was employed in combination with 150cc of a supported nickel catalyst (at the top of the reactor). The second catalyst in each of these examples was as follows:

Example 5—A 41% Ni-On-Alumina, 50% reduced nickel, as sphere

Example 6—A 50%/Ni-On-Alumina, 50% reduced nickel, as spheres

Example 7—A 50% Ni-on-mixed oxide support, 45% reduced nickel, as tablets

The results of these runs are summarized in Tables V to VII. All three catalyst combinations demonstrate substantial $CO_2$ suppression. Where The $H_2$ feed rate is 90 liters/hr, the $CO_2$ production is lowered into the range of 12–41 lbs/100M lb DEG converted.

TABLE V

| Reaction Temp. (°C.) | $H_2$ Feed Rate (l/hr) | DEG Conv. (%) | Yield (%) Basis DEG Converted | | Effluent Conc. $CO_2$ (ppm) | $CO_2$ (lbs) Per 100 M lbs DEG Converted |
|---|---|---|---|---|---|---|
| | | | Morpholine | DGA | | |
| 210 | 35 | 67.6 | 63.3 | 33.3 | 94 | 140 |
| 220 | 35 | 82.5 | 75.7 | 20.7 | 270 | 321 |
| 230 | 35 | 93.4 | 84.2 | 10.0 | 780 | 758 |
| 240 | 35 | 96.6 | 84.4 | 4.9 | 2675 | 2595 |
| 220 | 90 | 88.1 | 73.3 | 11.6 | 40 | 41 |
| 220 | 90 | 89.2 | 73.2 | 10.0 | 30 | 27 |

TABLE VI

| Reaction Temp. (°C.) | $H_2$ Feed Rate (l/hr) | DEG Conv. (%) | Yield (%) Basis DEG Converted | | Effluent Conc. $CO_2$ (ppm) | $CO_2$ (lbs) Per 100 M lbs DEG Converted |
|---|---|---|---|---|---|---|
| | | | Morpholine | DGA | | |
| 210 | 35 | 72.7 | 59.0 | 36.4 | 130 | 185 |
| 215 | 35 | 83.0 | 69.2 | 25.9 | 190 | 240 |
| 220 | 35 | 87.6 | 73.7 | 21.1 | 280 | 295 |
| 230 | 35 | 96.4 | 84.4 | 8.7 | 920 | 944 |
| 220 | 90 | 90.5 | 76.2 | 8.7 | 20 | 12 |
| 220 | 90 | 90.0 | 75.5 | 9.9 | 30 | 33 |

TABLE VII

| Reaction Temp (°C.) | $H_2$ Feed Rate (l/hr) | DEG Conv. (%) | Yield (%) Basis DEG Converted | | Effluent Conc. $CO_2$ (ppm) | $CO_2$ (lbs) Per 100 M lbs DEG Converted |
|---|---|---|---|---|---|---|
| | | | Morpholine | DGA | | |
| 210 | 35 | 71.7 | 58.4 | 36.6 | 103 | 150 |
| 215 | 35 | 81.8 | 67.9 | 26.8 | 184 | 240 |
| 220 | 35 | 88.7 | 76.7 | 18.4 | 300 | 356 |
| 230 | 35 | 96.6 | 85.7 | 7.7 | 830 | 847 |
| 220 | 90 | 91.4 | 75.3 | 5.9 | 26 | 30 |
| 220 | 90 | 90.3 | 76.3 | 7.1 | 22 | 27 |

COMPARATIVE EXAMPLE B

Following the operating procedures of Example 1, in this case the nickel-based dual catalyst system comprised 400cc of the nickel-copper-chromium oxide catalyst in combination with about 150cc of a nickel-copper-chromium-on-alumina catalyst containing about 47% nickel. Said catalyst combination was elevated for morpholine/DGA synthesis over a range of operating temperatures (210–250°). The results are summarized in Table VIII.

At about 80% DEG conversion, very little suppression of $CO_2$ was realized in comparison with Comparative Example A.

TABLE VIII

| Reaction Temp. (°C.) | $H_2$ Feed Rate (1/hr) | DEG Conv. (%) | Yield (%) Basis DEG Converted | | Effluent Conc. $CO_2$ (ppm) | $CO_2$ (lbs) Per 100 M lbs DEG Converted |
|---|---|---|---|---|---|---|
| | | | Morpholine | DGA | | |
| 210 | 35 | 62.9 | 63.7 | 33.6 | 105 | 172 |
| 220 | 35 | 75.5 | 70.0 | 25.2 | 265 | 365 |
| 230 | 35 | 87.7 | 82.2 | 12.7 | 890 | 1052 |
| 240 | 35 | 90.5 | 77.6 | 10.8 | 2840 | 3224 |
| 250 | 35 | 88.0 | 68.2 | 12.5 | 4060 | 4790 |

EXAMPLE 8

Following the operating procedures of Example 1, and using the same nickel-based dual catalyst system of nickel-copper-chromium oxides (400cc, bottom of reactor) and nickel-on-alumina (150cc, top of reactor), diethylene glycol amination was conducted over 500 hours using the same DEG, ammonia and hydrogen feed rates (1.2 lb/hr., 2.4 lb/hr, and 90 liters/hr respectively). Operating temperature and pressure were 215° C and 2200 psi, respectively.

Data from this 500 hour run are summarized in Table IX. It may be noted that over the life of this experiment:
(1) $CO_2$ production remains low (average 138 lb/100M lb DEG converted) and a factor of ca. 3.6 lower than in comparative Example A.
(2) The DEG conversion level remains high.
(3) There is no evidence of loss in morpholine plus DIGLYCOLAMINE ® amine yields, or the formation of unwanted by-products, in comparison with the data for Ni-Cu-Cr oxide catalyst alone, in comparative Example A.

TABLE IV

| Time On Stream (Hrs) | DEG Conversion (%) | Yield (%) Basis DEG Converted | | Effluent Conc. $CO_2$ (ppm) | $CO_2$ (lbs) per 100 M lbs. DEG Converted |
|---|---|---|---|---|---|
| | | Morpholine | DGA | | |
| 55 | 78.3 | 69.1 | 24.0 | 107 | 141 |
| 127 | 75.7 | 66.2 | 27.7 | 92 | 128 |
| 229 | 71.3 | 62.9 | 31.3 | 98 | 138 |
| 257 | 70.2 | 60.8 | 33.5 | 78 | 120 |
| 406 | 71.5 | 60.8 | 33.3 | 105 | 153 |
| 501 | 69.4 | 59.1 | 34.9 | 97 | 149 |

What is claimed is:

1. A process for simultaneously producing morpholine and DIGLYCOLAMINE ® amine while suppressing $CO_2$ formation comprising the steps of:
   reacting anhydrous diethylene glycol with ammonia in the presence of added hydrogen over a dual nickel-based catalyst system comprising a nickel-chromium oxide catalyst in combination with an oxide-supported nickel catalyst at a temperature of from about 150° C. to about 300° C. and a pressure of about 200 psig to about 5000 psig, and
   isolating said morpholine compound and said DIGLYCOLAMINE ® amine from the reaction products.

2. The process of claim 1 wherein the oxide-supported nickel catalyst comprises 10 to 80% nickel.

3. The process of claim 2 wherein the oxide support is selected from the group comprising alumina, silica, titania, zirconia, and magnesia, as well as mixtures thereof.

4. The process of claim 3 wherein the oxide support is alumina.

5. The process of claim 1 wherein the nickel-copper-chromium oxide component of the dual catalyst comprises:
   60 to 85 mole percent nickel,
   14 to 37 mole percent copper,
   1 to 6 mole percent chromium.

6. The process of claim 1 wherein the hydrogen flow is from 10 to 200 liters per lb of DEG converted.

7. The process of claim 4 wherein the nickel-on-alumina catalyst comprises 40 to 60% nickel.

8. In a process for simultaneously producing morpholine plus DIGLYCOLAMINE ® amine, the improvement of suppressing carbon dioxide formation by:
   reacting anhydrous diethylene glycol with ammonia in the presence of added hydrogen over a dual nickel based catalyst comprising a nickel-copper-chromium oxide catalyst comprising 72–78% nickel, 20–25% copper and 1–3% chromium in combination with a nickel-on-alumina catalyst containing 40–60% nickel, at a pressure of 200 psi to 5000 psi and a temperature from 200 to 250° C at hydrogen flow rates of from about 10 to 200 liters per lb of DEG converted, and
   isolating said morpholine and DIGLYCOLAMINE ® amine products from the reaction products.

9. The process of claim 8 wherein the ratio of nickel-copper-chromium oxide catalyst, to nickel-on-alumina catalyst, is in the range of 1:1 to 10:1 by volume.

* * * * *